United States Patent [19]

Harrington

[11] Patent Number: 4,911,712
[45] Date of Patent: Mar. 27, 1990

[54] MEDICAL LASER PROBE

[75] Inventor: James A. Harrington, Westlake Village, Calif.

[73] Assignee: Heraeus Lasersonics, Inc., Santa Clara, Calif.

[21] Appl. No.: 181,448

[22] Filed: Apr. 14, 1988

[51] Int. Cl.$^4$ .............................................. A61B 17/36
[52] U.S. Cl. ..................................... 606/14; 350/96.32
[58] Field of Search ...................... 128/303.1, 395–398, 128/6; 350/96.32, 96.2, 96.3; 372/64; 606/13, 14

[56] References Cited

U.S. PATENT DOCUMENTS

| | | | |
|---|---|---|---|
| 3,386,043 | 5/1968 | Marcatili et al. | 330/4.3 |
| 3,436,141 | 4/1969 | Comte | 350/96 |
| 3,441,337 | 4/1969 | Miller | 350/96 |
| 3,467,098 | 9/1969 | Ayres | 128/303.1 |
| 3,528,424 | 9/1970 | Ayres | 128/303.1 |
| 3,583,786 | 6/1971 | Marcatili | 350/96 |
| 3,700,900 | 10/1972 | Herleikson | 250/199 |
| 3,788,728 | 1/1974 | Nassenstein et al. | 350/96 |
| 3,864,019 | 2/1975 | Smolinski et al. | 350/96 |
| 3,900,245 | 8/1975 | Dyott et al. | 350/96 |
| 3,905,676 | 9/1975 | Ulrich | 350/96 |
| 3,912,363 | 10/1975 | Hammer | 350/96 |
| 3,924,020 | 12/1975 | Duffy et al. | 427/162 |
| 3,930,714 | 1/1976 | Dyott | 350/96 |
| 3,932,162 | 1/1976 | Blankenship | 65/3 |
| 3,933,453 | 1/1976 | Burke et al. | 65/3 |
| 3,957,342 | 5/1976 | Newns et al. | 350/96 |
| 3,971,645 | 7/1976 | Bachmann et al. | 65/3 |
| 3,973,828 | 8/1976 | Onoda et al. | 350/96 |
| 3,980,459 | 9/1976 | Li | 65/18 |
| 3,982,541 | 9/1976 | L'Esperance | 128/395 |
| 4,009,014 | 2/1977 | Black et al. | 65/3 |
| 4,011,403 | 3/1977 | Epstein et al. | 358/209 |
| 4,019,051 | 4/1977 | Miller | 250/227 |
| 4,033,667 | 7/1977 | Fleming | 350/96 |
| 4,054,366 | 10/1977 | Barnoski et al. | 350/96 |
| 4,060,308 | 11/1977 | Barnoski et al. | 350/96 |
| 4,067,709 | 1/1978 | Stanton | 65/3 |
| 4,068,920 | 1/1978 | Bass et al. | 350/96 |
| 4,076,375 | 2/1978 | Muska et al. | 350/96.15 |
| 4,077,699 | 3/1978 | Dyott et al. | 350/96.34 |
| 4,082,420 | 4/1978 | Shiraishi et al. | 350/96.31 |
| 4,091,334 | 5/1978 | Sechi | 330/287 |

(List continued on next page.)

FOREIGN PATENT DOCUMENTS 0196519 10/1986 European Pat. Off. ......... 128/303.1

OTHER PUBLICATIONS

Jenkins & Devereux, "Dispersion Phenomena in Hollow Alumina Waveguides", IEEE Journal of Quantum Electronics, 1985, pp. 1722–1727.
Baggish & Eibakry, "A Flexible $CO_2$ Laser Fiber for Operative Laparoscopy", Fertility and Sterility, Jul. 1986, pp. 15–20.
Harrington, "Medical Needs Drive IR Fiber Development", Photonics Spectra, Jul. 1987, pp. 61–63.
Morikawa & Shimade, "Hollow-Core Oxide-Glass Cladding Optical Fibers for Middle Infrared Region", Journal of Applied Physics, Jul. 1981, pp. 4467–4471.
Hall, Gorton & Jenkins, "10-$\mu$m Propagation Losses in Hollow Dielectric Waveguides", Journal of Applied Physics, Mar. 1977, pp. 1212–1216.
Aronson, "Optical Constants of Monoclinic Anisotropic Crystals: Orthoclase", Spectrochimica Acta, 1986, pp. 187–190.
Aronson & Emslie, "Effective Optical Constants of Anisotropic Materials", Applied Optics, Dec. 1980, pp. 4128–4129.
Aronson, Emslie, Smith & Strong, "Derivation of the Optical Constants of Anisotropic Materials", U.S. Army Research Office Publication, Jul. 1985, pp. 0–28.
Croitoru, Dro & Mendlovic, "Plastic Hollow Tubes as Waveguides for IR Radiation", SPIE's O-E LASE, Jan. 1988, 5 pages.

Primary Examiner—Max Hindenburg
Attorney, Agent, or Firm—Flehr, Hohbach, Test, Albritton & Herbert

[57] ABSTRACT

A probe is described for delivering $CO_2$ radiation to a desired site. Such probe includes an n<1 optical guide made of sapphire tubing. In one embodiment, the probe includes a disposable tip.

14 Claims, 2 Drawing Sheets

U.S. PATENT DOCUMENTS

| | | | |
|---|---|---|---|
| 4,099,837 | 7/1978 | Vazirani | 350/96.29 |
| 4,111,525 | 9/1978 | Kaminow et al. | 350/96.31 |
| 4,114,112 | 9/1978 | Epstein et al. | 331/94.5 |
| 4,123,138 | 10/1978 | Morrison | 350/96.21 |
| 4,124,272 | 11/1978 | Henderson et al. | 350/96.21 |
| 4,126,136 | 11/1978 | Auth et al. | 128/303.1 |
| 4,128,299 | 12/1978 | Maher | 350/96.13 |
| 4,130,343 | 12/1978 | Miller et al. | 350/96.15 |
| 4,135,780 | 1/1979 | Dyott | 350/96.15 |
| 4,146,298 | 3/1979 | Szczepanek | 350/96.15 |
| 4,169,976 | 10/1979 | Cirri | 219/121 LM |
| 4,170,997 | 10/1979 | Pinnow et al. | 128/395 |
| 4,172,106 | 10/1979 | Lewis | 264/1 |
| 4,173,393 | 11/1979 | Maurer | 350/96.34 |
| 4,181,515 | 1/1980 | Dyott et al. | 65/3 |
| 4,194,808 | 3/1980 | Marhic et al. | 350/96.32 |
| 4,212,537 | 7/1980 | Golob et al. | 356/73.1 |
| 4,222,631 | 9/1980 | Olshansky | 350/96.31 |
| 4,230,993 | 10/1980 | Cirri | 331/94.5 |
| 4,248,614 | 2/1981 | Scherer | 65/3 |
| 4,265,515 | 5/1981 | Kao | 350/96.33 |
| 4,272,854 | 6/1981 | Pleibel et al. | 65/2 |
| 4,277,272 | 7/1981 | Schneider | 65/3 |
| 4,283,213 | 8/1981 | Akers et al. | 65/3 |
| 4,290,668 | 9/1981 | Ellis et al. | 350/96.2 |
| 4,295,870 | 10/1981 | Schneider et al. | 65/3 |
| 4,300,816 | 11/1981 | Snitzer et al. | 350/96.33 |
| 4,302,232 | 11/1981 | Schneider et al. | 65/3 |
| 4,310,339 | 1/1982 | Blankenship | 65/3 |
| 4,341,441 | 7/1982 | Lighty et al. | 350/96.30 |
| 4,349,843 | 9/1982 | Laakmann et al. | 358/206 |
| 4,351,585 | 9/1982 | Winzer et al. | 350/96.15 |
| 4,360,250 | 11/1982 | Payne et al. | 350/96.30 |
| 4,361,139 | 11/1982 | Takagi | 128/6 |
| 4,372,767 | 2/1983 | Maklad | 65/3 |
| 4,373,202 | 2/1983 | Laakmann et al. | 372/64 |
| 4,377,322 | 3/1983 | Ransley et al. | 350/96.2 |
| 4,385,802 | 5/1983 | Blaszyk et al. | 350/96.33 |
| 4,393,506 | 7/1983 | Laakman et al. | 372/59 |
| 4,401,363 | 8/1983 | Barlow | 350/96.3 |
| 4,407,561 | 10/1983 | Wysocki | 350/96.3 |
| 4,418,984 | 12/1983 | Wysocki et al. | 350/96.33 |
| 4,422,733 | 12/1983 | Kikuchi et al. | 350/413 |
| 4,423,925 | 1/1984 | Dabby et al. | 350/96.31 |
| 4,427,260 | 1/1984 | Puech et al. | 350/96.14 |
| 4,432,601 | 2/1984 | Mannschke | 350/96.19 |
| 4,451,116 | 5/1984 | Pinnow et al. | 350/96.34 |
| 4,453,803 | 6/1984 | Hidaka et al. | 350/96.32 |
| 4,456,330 | 6/1984 | Bludau | 350/96.18 |
| 4,465,336 | 8/1984 | Huber et al. | 350/96.30 |
| 4,473,074 | 9/1984 | Vassiliadis | 128/303.1 |
| 4,488,307 | 12/1984 | Garmire et al. | 372/50 |
| 4,500,167 | 2/1985 | Mori | 350/96.32 |
| 4,538,609 | 9/1985 | Takenaka et al. | 128/303.1 |
| 4,557,566 | 12/1985 | Kikuchi et al. | 350/413 |
| 4,564,417 | 1/1986 | Schoen et al. | 156/633 |
| 4,566,753 | 1/1986 | Mannschke | 350/96.16 |
| 4,610,505 | 9/1986 | Becker et al. | 350/96.23 |
| 4,643,514 | 2/1987 | Raviv et al. | 350/3 |
| 4,643,751 | 2/1987 | Abe | 65/3 |
| 4,652,083 | 3/1987 | Laakmann | 350/96.32 |
| 4,657,341 | 4/1987 | Sammueller | 350/96.22 |
| 4,659,175 | 4/1987 | Wilde | 350/96.20 |
| 4,664,473 | 5/1987 | Gannon | 350/96.33 |
| 4,676,820 | 6/1987 | Le Sergent et al. | 65/3 |

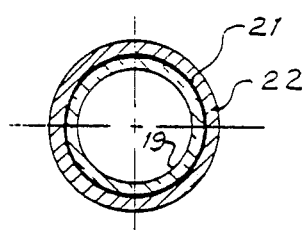
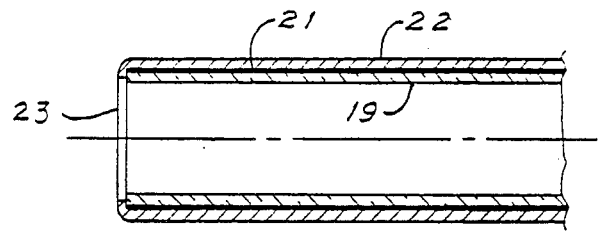
FIG. 3    FIG. 4
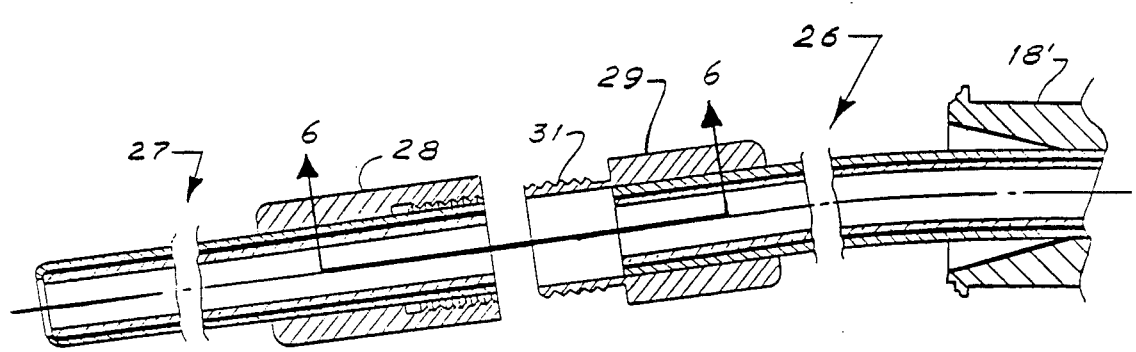
FIG. 5
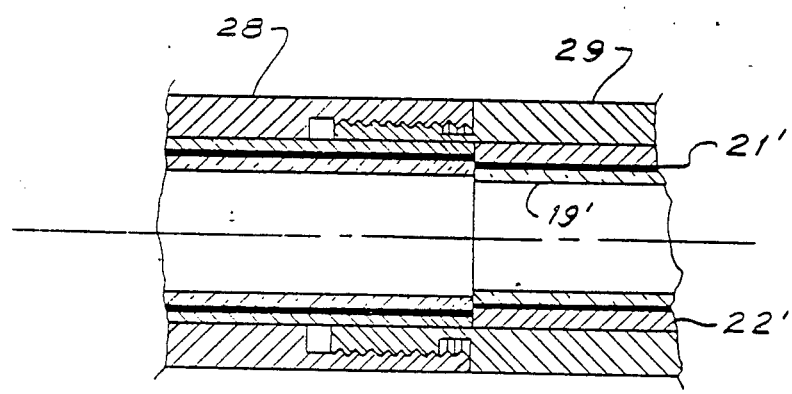
FIG. 6

MEDICAL LASER PROBE

BACKGROUND OF THE INVENTION

The present invention relates to laser systems and, more particularly, to a probe for delivering 10.6 micron wavelength radiation and a method for such delivery.

$CO_2$ (carbon dioxide) laser radiation is of major interest to the medical community because of the ability of the principle component of its output radiation, 10.6 microns in wavelength, to cut and/or ablate both normal and abnormal mammalian tissue when delivered at appropriate power levels. However, delivery systems for conveying the same to a mammalian tissue site have been less than ideal—this is particularly true for internal delivery. As pointed out in assignee's co-pending patent application Ser. No. 07/164,236 filed Mar. 4, 1988 entitled "DELIVERY ARRANGEMENT FOR A LASER MEDICAL SYSTEM" and naming the applicant hereof as an inventor, the delivery system must be both flexible and preferably sufficiently small at its distal end for cavity insertion and intracavity manipulation. A critical component in such delivery is the optical waveguide which directs the radiation from a source of the same to adjacent the desired mammalian tissue site. (If the waveguide is connected directly to a $CO_2$ laser to receive its output, the source is the laser itself, whereas if the delivery system is a multi-component system such as described in co-pending application Ser. No. 07/164,236, the source can be another component of the system.)

The characteristics that are desired in a medical probe for $CO_2$ laser radiation are known. It is desirable that it be small as mentioned above, i.e., small in dimension in the direction normal to the direction of guiding. Surgeons prefer that the greatest dimension in such direction of any part which may be inserted internally into a body, be no greater than 1 millimeter. It is also quite important that it be flexible, i.e., capable of being flexed, without major variations in its transmission capability. In connection with the latter, a surgeon has to be able to expect basically the same output power from the probe irrespective of variations in probe flexing. Moreover its is important that the portion of the guide, the operative part of the probe, which is to be inserted into a body be fairly long, e.g., about 75 centimeters in length. This means that the transmission loss per unit of length has to be minimized.

Much effort and investigation has been undertaken in an effort to provide an appropriate medical probe. In this connection, efforts have been made to extend the wavelength range of dielectric optical fibers of the type used with other wavelengths formed by extruding crystals or drawing special glasses. For example, reference is made to the paper entitled "Hollow-Core Oxide-Glass Cladding Optical Fibers for Middle Infrared Region" (July 1981) by T. Hidaka, et al., published in *THE JOURNAL OF APPLIED PHYSICS*, Vol. 52, No. 7, page 4467 et seq. These efforts, though, have not been satisfactory since such materials have transmission loss for $CO_2$ radiation. Such transmission loss is particularly significant when the materials form bent structures, such as curved probes, since much of the input radiation is absorbed. The paper entitled "Fiber Optic Trends" authored by the instant inventor and appearing on page 51 in the July 1987 issue of *PHOTONICS SPECTRA* provides a basic overview of the developments with respect to IR fibers (optical waveguides for $CO_2$ radiation). As brought out in such paper, $CO_2$ radiation transmission in most of such fibers is significantly decreased when the fiber is flexed to a small bend radius. An investigation with respect to use of a particular metal probe which is dielectrically coated is described in the paper entitled "A Flexible $CO_2$ Laser Fiber for Operative Laparoscopy" (July 1986) by Baggish, et al. appearing in *FERTILITY AND STERILITY*, volume 46, page 16. While it is stated that such metal IR fiber is "flexible," the effect of flexing on transmission is not discussed. It is expected to be great based on other metal waveguides, though, since a metal is quite lossy and differential flexing will result in significantly great differential absorption. Moreover, the lossy nature of such a guide will limit its overall length.

There is an anomalous dispersion phenomenon that is associated with transmission of 10.6 micron radiation through certain non-metallic, hollow waveguides. As pointed out in the paper entitled "Dispersion Phenomena in Hollow Alumina Waveguides" (1985) authored by Jenkins, et al. and appearing at pages 1722 et seq. in the IEEE Journal of Quantum Electronics, Vol. QE-21, it has been discovered that alumina waveguides have an abrupt change in attenuation which is directly related to the wavelength of the radiation which is transmitted. It has been found that the attenuation of 10.6 micron radiation by a hollow air core alumina waveguide is significantly lower than it is for other longer or shorter wavelengths, such as 9.6 micron radiation. This phenomenon has been associated with the index of refraction (n) of the alumina relative to the wavelength. That is, this relatively unexpected phenomenon has been associated with the index of refraction of the alumina becoming less than that of the air core over a short range of wavelengths.

Most polycrystalline materials satisfactory for $n<1$ hollow guides are too brittle to provide flexing. Probe constructions using polycrystalline material as a cladding in which some flexing can be achieved have been considered. For example, it has been considered to provide a thin coating or layer of a polycrystalline material within an otherwise flexible substrate tubing. While such a construction may permit flexing, relatively high transmission losses would be expected due to the polycrystalline nature of the coating.

Although there has been much investigation and effort to arrive at a satisfactory probe for delivering $CO_2$ radiation, to date these efforts have not produced an entirely satisfactory probe or method of delivering 10.6 micron radiation to a mammalian tissue site.

SUMMARY OF THE INVENTION

It has been found that a hollow waveguide in which the index of refraction of the cladding of the waveguide (the material providing the cladding) is less than that of the core can be made flexible and yet transmit 10.6 micron radiation upon flexing without appreciable loss if the cladding material is a single crystal material. The core of a hollow waveguide in most instances is air having an index of refraction of 1. Thus, a hollow waveguide of the type to which the invention relates is commonly referred to as a "$n<1$" waveguide.

The difference in transmission losses of 10.6 micron radiation upon flexing when the cladding material is a monocrystalline material as opposed to a polycrystalline material, is unexpected. While the reasons for this difference are not truly understood, it is thought that it may have to do with the reflectance at the cladding-core interface. A polycrystalline material will have a random orientation of randomly sized grains at such interface relative to the electrical field of the radiation being transmitted, whereas a single crystal structure is, in essence, a single gram having a regular array of atoms. This surface configuration at the cladding-core interface will result in a surface roughness if the material is a polycrystalline material that will scatter and absorb radiation. The transmission loss that is caused by this surface roughness is magnified when the material is flexed since flexure necessarily results in many more surface reflections to provide transmission. Furthermore, each different flexing configuration will present a different number of internal interactions between the cladding and the radiation, with the result that the transmission loss will vary from one flex configuration to another. In contrast, a single crystal cladding-core interface will present a regular, smooth surface to the radiation and the greater number of reflections associated with flexing does not result in significant transmission loss. Also, some of the polycrystalline materials which have been considered, including alumina, are ceramics, and the binder used with the same acts as an impurity and results in absorption. Again, flexing magnifies the effect of the presence of an impurity because of the varying, greater number of reflections.

Most desirably, the single crystal material is sapphire. It has been found that when tubular sapphire having a length of 91 centimeters for a probe was flexed, there was essentially no material difference in transmission loss of 10.6 micron radiation compared to an unflexed tube. This was found to be true even when the sapphire tube was bent to a radius of curvature of 28 centimeters. (Such probe sapphire tube had an internal diameter of 400 microns.) Moreover, the overall transmission loss was only 3.5 dB/m. Also when the $n<1$ hollow waveguide is a sapphire tube, the body of the probe itself acts as a waveguide for visible radiation having a wavelength of 0.63 microns emanating from a HeNe (helium-neon) laser. Thus, the tubular sapphire provides two functions - it acts as the desired flexible single crystal probe for 10.6 radiation and acts to furnish the necessary light to illuminate a site. Even in those constructions in which the hollow waveguide cladding is not sapphire it is desirable that the cladding construction be transparent or translucent to visible radiation and is a guide for directing illuminating radiation to the site.

As another aspect of the instant invention, the optical guide is provided in two sections, a main optical guide section and a replaceable or disposable tip section. Both sections most desirably are hollow, air core guides through which a purge gas, such as nitrogen, can be passed during use of the same. Also, with such an arrangement the tip section can be replaced when it becomes contaminated or clogged due to its proximity to a site to which the radiation is to be directed.

It has been found that the coupling loss between the two sections where they mate can be minimized. To this end, when both sections are hollow waveguide sections it is preferable that the inner diameter of the tip section waveguide be greater than that of the main body section so that misalignment between the two has little effect on the ability to guide radiation at the joint between such sections.

The invention includes other features and advantages which will be described or will become apparent from the following more detailed description.

BRIEF DESCRIPTION OF THE DRAWINGS

With reference to the accompanying two sheets of drawing:

FIG. 3 is a sectional view taken on a plane indicated by the lines 3—3 in FIG. 2;

FIG. 4 is an enlarged sectional view of the encircled tip portion of the embodiment of FIG. 2;

FIG. 5 is an enlarged sectional and broken away partial view of an alternate embodiment of the instant invention having a main body section and a tip section, showing such sections separated from one another; and FIG. 6 is an enlarged view of the joint between the two sections of the embodiment of FIG. 5 with the sections connected together.

DETAILED DESCRIPTION OF PREFERRED EMBODIMENTS

Figure 1:
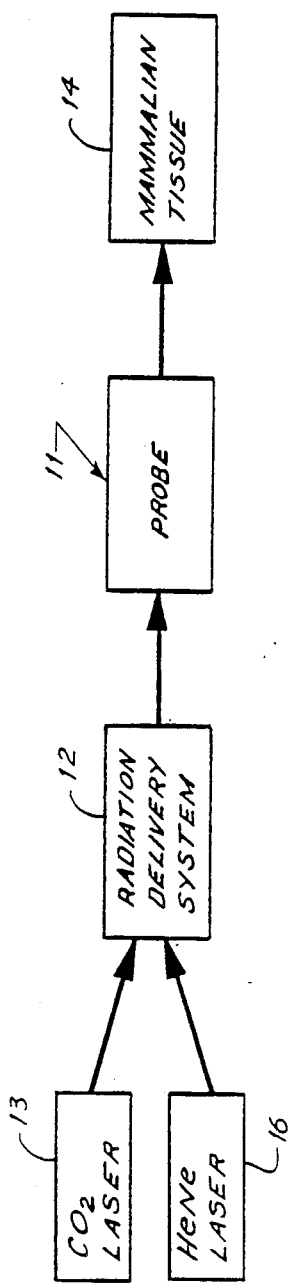
FIG. 1 is a schematic block diagram showing the relationship of a probe of the instant invention to the remainder of a laser medical system and a mammalian tissue to be treated.

FIG. 1 is a schematic illustration of the relationship of a probe of the invention to a laser medical system and mammalian tissue to be treated. The medical probe, generally referred to by the reference numeral 11, is illustrated receiving radiation from a source of such radiation represented as radiation delivery system 12. Such system receives 10.6 micron coherent radiation from a $CO_2$ laser 13 to be delivered to an operating site on mammalian tissue represented at 14. It also receives illuminating 0.63 micron radiation (light) from a HeNe laser represented at 16 to be delivered to the site.

It will be recognized by those skilled in the art that in some situations illuminating radiation does not have to be delivered to the surgical or other site. Moreover, there are other ways of obtaining and/or delivering illumination to a site when it is desired. It also will be recognized by those skilled in the art that it is not necessary in some situations that there be a radiation delivery system between the probe and the laser, particularly when the probe is relatively long. That is, the probe can be connected directly to the head of the laser which produces the coherent radiation of interest.

Figure 2:
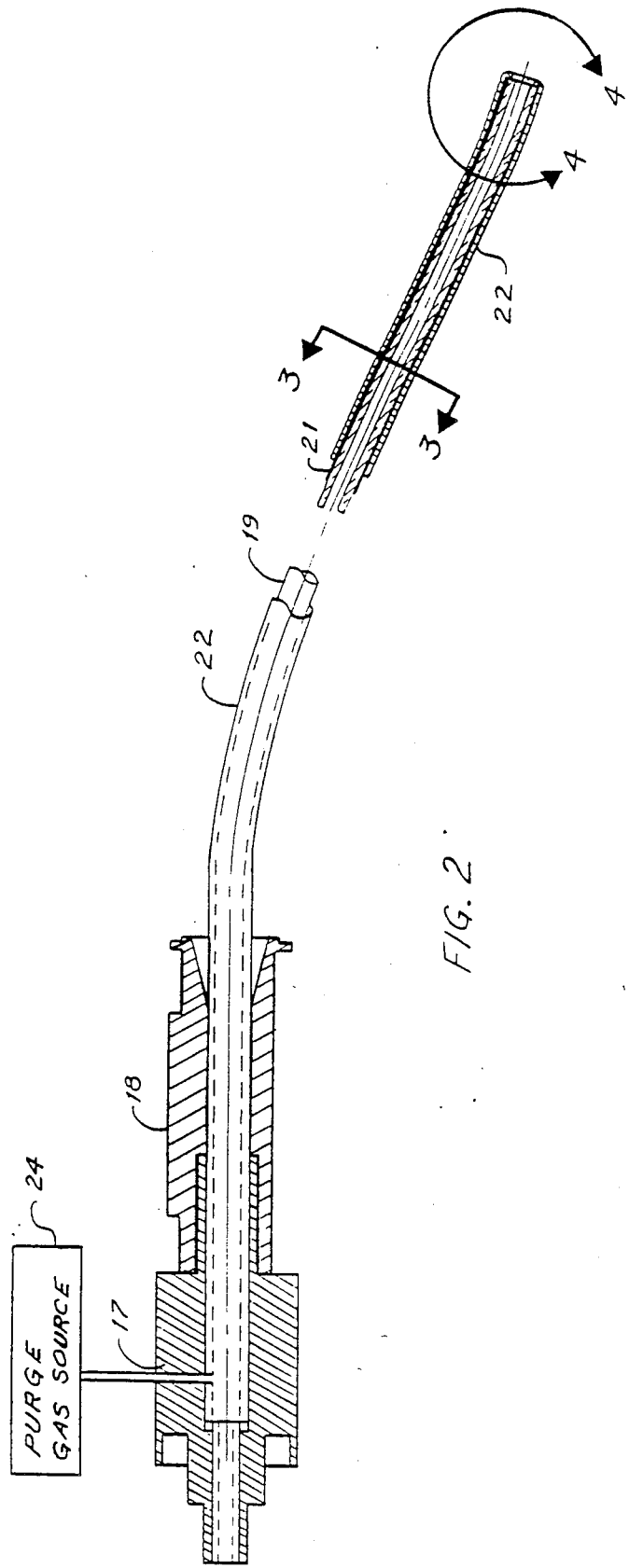
FIG. 2 is an enlarged sectional and broken away view of a preferred embodiment of the probe of the invention.

A preferred embodiment of the probe of the invention is illustrated in detail in FIGS. 2–4. Such embodiment includes a standard connector structure 17. This embodiment is designed to convey both the desired 10.6 micron operating radiation and illuminating radiation. Thus, connector 17 is capable of connecting the probe appropriately to a delivery system to receive both 10.6 micron coherent radiation in the hollow core of the waveguide tube which will be described, as well as 0.63 micron illuminating coherent radiation in its body. The probe further includes a body fitting 18 which acts as physical structure registering with the connector 17 as illustrated.

The principle component of the probe is a sapphire tube, generally referred to by the reference numeral 19. Tube 19 has an inner diameter (ID) of 400 microns, an outer diameter (OD) of 575 microns, and is 91 centimeters long. It functionally acts as the waveguide cladding for the 10.6 micron radiation and has an index of refraction of approximately 0.7 for 10.6 micron radiation at such wavelength, whereas the core of the guide (air) has an index of refraction of 1 for such radiation. The result is that the sapphire tube of the preferred embodiment of the invention is an $n<1$ guide for 10.6 micron radiation. It extends as illustrated through the connector 17 to receive such radiation from the delivery system. The tube extension also permits receipt by the translucent sapphire body itself, i.e., between its ID and OD, of illuminating 0.63 micron radiation originated by HeNe laser 16 to follow the 10.6 micron radiation to the site. The illuminating radiation will form a circle circumscribing the 10.6 radiation at the tissue site. This will simplify visual identification of the location of the principle radiation and is a natural consequence of the tubular shape of the sapphire.

Most importantly, sapphire tube 19 is monocrystalline and is flexible, and it has been found that flexing (bending) of such single crystal material to a degree typically encountered in surgery, does not result in significant changes in the power of 10.6 micron radiation which is transmitted. It therefore enables the probe of the invention to be used quite reliably. That is, a user of the probe, such as an operating surgeon, will accurately have at the free or distal end of the probe an amount of output radiation that does not vary materially irrespective of any flexing or bending of the probe which may be necessary during an operation. In this connection, it has been found that less than 30% transmission loss deviation can be expected for the tube having the dimensions set forth above when flexed to a 28 centimeter bend radius. (In contrast, one can expect about a six-fold increase in the transmission loses when an $n<1$ hollow $GeO_2$ tube is bent to about a 50 centimeter radius.) Moreover, when planning an operation a surgeon can count on differing bending requirements not materially affecting the power of radiation which will be delivered.

The c-axis of the crystal lattice structure extends in the direction of guiding by the tubing, i.e., along its optic axis. This is a high strength orientation that is selected to prevent the cleavage plane from being perpendicular to the optic axis. In aligning the c-axis parallel to the optic axis, one keeps the modulus of rupture high and minimizes fracture due to cleavage.

The absorption loss in an air core hollow waveguide of radiation having a particular wavelength is directly proportional to the value of k, the extinction coefficient of the cladding material. That is, the complex refractive index N of the cladding material is equal to $n-ik$, where n is the refractive index and k is the extinction coefficient. It is particularly important that the value of k be small at the wavelength of interest when one considers loss due to bending, because the angle of incidence of the radiation is greater in a bent or flexed guide than it is in a straight guide and there are more internal reflections in the former, resulting in a longer path length. It will be appreciated that if absorption loss of 10.6 micron radiation is kept to a minimum, the significance of changes in the absorption loss caused by bending will be minimized. Sapphire has an extinction coefficient of 0.06, making it particularly attractive as the material for tube 19. As a comparison, the extinction coefficient for a particular $GeO_2$-based glass tubing that has been proposed for a $n<1$ waveguide for $CO_2$ radiation is 0.82. Since the absorption loss is proportional to the k value and since the k value for such glass is over ten times that of sapphire, one can naturally expect a significantly greater loss on flexing tubing of such $GeO_2$ based glass tubing than on flexing sapphire tubing of comparable dimensions.

One other advantage of sapphire tubing attributable to its single crystal nature is the fact that upon flexing, it does not change the mode makeup of the 10.6 micron radiation that it guides. That is, if a single mode, such as the $TEM_{oo}$ mode, of 10.6 radiation is fed into the same, the output radiation also will be of such single mode irrespective of reasonable flexing. In contrast, if hollow waveguides of polycrystalline or amorphous materials are flexed or built with a fixed curve, they will typically separate a single mode of 10.6 micron radiation into multiple, higher order modes. Each of these modes will be directed by the guide to different spot locations, with the result that the transmitted power will be spread out rather than concentrated at a single spot as desired. Moreover, sapphire neither loses its structural integrity nor its optical properties when exposed to high temperatures, e.g., 1500° C., such as can be expected if radiation cannot exit the end of the probe because of, for example, clogging or the like. It also is chemically inert and biocompatible.

The probe of the invention illustrated in FIGS. 2-4 also includes a coating 21 of a material, such as a tetrafluoroethylene fluorocarbon polymer or fluorinated ethylene-propylene resin sold by, among others, E. I. du Pont de Nemours and Co. sold under the trademark Teflon. Such coating is a part of a protective covering for the tube 19 and acts as a buffer between sapphire tubing 19 and an exterior protective housing 22. If tubing 19 should fracture, coating 21 will also tend to maintain adjacent ends of the same in abutment to reduce transmission losses caused by such breakage. Protective housing 22 is most desirably flexible so that it will not interfere with the inherent flexibility of the tubing 19. In this connection, it can be formed of thin walled, stainless steel hypodermic tubing.

The protective covering, including coating 21 and housing 22, extends for substantially the full length of the tubing. In this connection, it extends through the fitting 18 into the connector 17 as illustrated.

In some situations, neither housing 22 nor coating 21 are needed, i.e., when sapphire tubing 19 has enough structural strength to withstand normal usage and provide adequate structural resistance to withstand the environment within which the probe will be used. In other situations, the invention can be employed with only a housing or a coating, but not both.

As a significant feature of the invention the housing 22 of the protective outer covering is shaped at the exit end of the waveguide to prevent the sapphire tubing from exiting the probe at such end. A surgeon or other user of the probe therefore need not be concerned that breakage of the tubing will result in pieces of the same exiting the probe at the site to which the radiation is being directed. In this connection, it must be remembered that because the tubing is monocrystalline any breakage of the same will be along a regular cleavage plane, rather than be a shattering. FIG. 4 illustrates the exit end shape of the outer housing covering which is responsible for preventing exiting of the tubing guide at such location. That is, housing 22 is directed inwardly of the probe structure adjacent the radiation exit end 23 to overlap the end of tubing 19. While, it does not overlap the tubing end to such a degree that it interferes with exiting of the 10.6 micron radiation from such tubing, it will restrict to some degree exiting from the same of illuminating radiation carried by the body of the tubing.

It will be seen that with this construction, if the optical guide portion 19 should break along its length it will be prevented from exiting the probe at the radiation exit end.

An advantage of using the hollow guide is that a purging gas, such as nitrogen, can be passed through the same for delivery along with the radiation to the site. The gas can be introduced into the interior of the guide through, for example, the connector 17 as schematically illustrated at 24.

The protective housing 22 has an outer diameter of 1.0 millimeters and an inner diameter of 0.9 millimeters. Coating 19 is provided with a thickness of 0.15 millimeters to assure that there is a tight structural fit between the actual optical guide and its protective covering.

It will be appreciated from the above description that the probe of the invention satisfies the major requirements of surgeons. That is, it delivers the desired 10.6 micron radiation to a tissue site with a minimum of transmission loss while yet being flexible. (In this connection, it is uniformly flexible along its length except, of course, for that portion of its length which is taken up by the connector 17 and fitting 18.) Most importantly, the power output of the probe does not materially change when the degree of flexing changes.

The embodiment of the probe illustrated in FIGS. 5 and 6 adds another desirable feature to the features discussed above. Such probe has two sections, a main optical guide section 26 and a tip section 27. The main section is designed to receive the radiation and, in this connection, includes both a fitting 18' and a connector (not shown) which are the same as the fitting and connector in the earlier described embodiment. The tip section is designed to receive the radiation from the main guide and guide the same to adjacent the desired site. Such tip section is separable from the main section to thereby become, in essence, a disposable tip. That is, a surgeon may replace the tip on a guide while retaining the main portion of the probe for reuse.

A tip coupling made up of two mating cylindrical parts 28 and 29 is provided to facilitate separable connection. The tip part 28 of the coupling includes a threaded bore circumscribing the probe, and the main part 29 has a threaded cylindrical extension 31 designed to threadably mate within such bore. As illustrated in FIG. 6, the parts 28 and 29 can be threaded together to tightly mate with one another. The remainder of both sections of the probe having sapphire tubing 19' and a protective outer covering comprising a coating 21' and a housing 22' as described above, abut tightly against one another when the coupling parts also abut one another. (It will be noted that this embodiment of the invention is the same, except as described, as the embodiment illustrated in FIGS. 2-4.)

The inner diameter of the hollow waveguide of the tip section is greater than that of the main body section. This enhances the lack of coupling loss at the joint. That is, misalignment between the two sections at the joint when they are coupled together is accommodated, so that there is no guide discontinuity at the joint facing radiation travelling between the two sections.

For example, in one hollow waveguide embodiment of this aspect of the invention the guide of the tip section had an ID of 1.05 millimeters, whereas the main section had an ID of 0.8 millimeters. It will be recognized by those skilled in the art that it is not necessary that the material of the hollow guide of the tip section be the same as that of the main body section. In this connection, such tip section could be inflexible (assuming, of course, that it is relatively short in length) and have a cladding of another material. As long as such tip section is reasonably short it can be of a polycrystalline material, such as alumina, or even of an amorphous material. While such tip section could have a different guiding structure altogether than the main section, most desirably it also is a hollow wave guide so that a purging gas can be passed through both it and the main section. In this connection, it will be recognized that a purging gas system such as in the earlier described embodiment can be utilized with the same.

Although the invention has been described in connection with preferred embodiments thereof, it would be appreciated by those skilled in the art that various modifications and changes can be made. For example, although it has been described in connection with a single material making up the body of the cladding, it will be recognized that it could be made up of a flexible tubular substrate, such as a thin tubing of quartz, having an internal coating of a monocrystalline material formed, for example, by CVD deposition. And although the preferred embodiment utilizes monocrystalline sapphire for the optical guide, it will be appreciated that there are other materials which also have monocrystalline forms that can be used to form hollow $n<1$ guides such as silicon carbide (SiC); aluminum nitride (AlN) ; and germanium oxide ($GeO_2$). Moreover, while the invention has been described in connection with its use in a medical environment, it will be recognized that it may well find use in other environments, such as for welding or communications. It is therefore intended that the coverage afforded applicant be limited only by the claims and their equivalents.

What I claim is:

1. A probe for delivering radiation having a wavelength of 10.6 microns from a source of such radiation to adjacent a site comprising, in combination:
    A. A main optical waveguide section for receiving said radiation and guiding the same from a source to an opposite end thereof, said main section including a waveguide cladding of an $n<1$ material and a waveguide core;
    B. A tip optical waveguide section for receiving radiation from said opposite end of said main guide section and guiding the same to adjacent said site, said tip section also including a waveguide cladding of an $n<1$ material and a core; and
    C. Said main and tip sections being separably connectable together with the cladding and core of one tightly abutting respectively the cladding and core of the other for passage of said radiation therebetween, the claddings of said two sections being disengaged from one another when said sections are disconnected.

2. A probe according to claim 1 wherein said main optical guide section is flexible along substantially its full length.

3. A probe according to claim 1 wherein said probe is a medical probe and said site is a mammalian tissue site, further including a connector as part of said main optical guide section for receiving said radiation from a medical delivery system.

4. A probe according to claim 1 wherein at least one of said sections is a hollow, air core waveguide.

5. A probe according to claim 4 wherein the waveguide cladding of said one section is sapphire.

6. A probe according to claim 4 wherein both of said sections are hollow, air core waveguides.

7. A probe according to claim 6 further including means for passing a purging gas through both of said hollow, air core waveguide sections.

8. A probe according to claim 6 wherein the inner diameter of the cladding of said hollow waveguide tip section is greater than that of the cladding of said main section.

9. A probe for delivering radiation having a wavelength of 10.6 microns from a source of such radiation to adjacent a site comprising, in combination;
   A. An optical hollow waveguide having a source and for receiving said radiation and guiding the same from a source to a radiation exit end, said optical waveguide including a waveguide cladding of an n<1 material and a core;
   B. A protective outer covering for said optical guide extending substantially the full length thereof;
   C. A connector at the source end of said guide for connecting said guide with said protective covering thereon to a source of said radiation; and
   D. Said protective outer covering being directed inwardly at the opposite end of said waveguide to overlap a portion of said cladding and prevent the same from exiting said probe at said radiation exit end.

10. A probe according to claim 9 wherein said hollow optical guide is tubular sapphire.

11. A probe according to claim 9 wherein said hollow guide and protective outer covering therefor are provided in two separable sections, a main guiding section for receiving said radiation and a disposable tip section having said radiation exit end for delivering said radiation to said site, and said inwardly directed portion of said outer covering is provided at the exit end of said tip section.

12. A probe according to claim 11 wherein said waveguide sections tightly abut against one another to minimize radiation coupling loss therebetween.

13. A probe according to claim 9 wherein said protective outer covering has two parts, an exterior metallic part and an inner coating of a tetrafluoroethylene polymer or a fluorinated ethylene-propylene resin.

14. A probe according to claim 13 wherein said hollow optical guide and said protective outer covering are flexible.

* * * * *